United States Patent
Di Poian et al.

(10) Patent No.: US 11,457,853 B2
(45) Date of Patent: Oct. 4, 2022

(54) METHODS AND SYSTEMS FOR AUTOMATICALLY DETECTING EVENTS BASED ON ECG SIGNALS DETERMINED FROM COMPRESSED SENSED MEASUREMENTS

(71) Applicants: Emory University, Atlanta, GA (US); Universita degli Studi di Udine, Udine (IT)

(72) Inventors: Giulia Di Poian, Belluro (IT); Roberto Rinaldo, Venice (IT); Gari Clifford, Decatur, GA (US)

(73) Assignees: Emory University, Atlanta, GA (US); Universita degli Studi di Udine, Udine (IT)

( * ) Notice: Subject to any disclaimer, the term of this patent is extended or adjusted under 35 U.S.C. 154(b) by 137 days.

(21) Appl. No.: 16/496,917

(22) PCT Filed: Mar. 22, 2018

(86) PCT No.: PCT/US2018/023853
§ 371 (c)(1),
(2) Date: Sep. 23, 2019

(87) PCT Pub. No.: WO2018/175785
PCT Pub. Date: Sep. 27, 2018

(65) Prior Publication Data
US 2020/0085330 A1    Mar. 19, 2020

Related U.S. Application Data

(60) Provisional application No. 62/475,198, filed on Mar. 22, 2017.

(51) Int. Cl.
*A61B 5/36*    (2021.01)
*A61B 5/361*   (2021.01)
(Continued)

(52) U.S. Cl.
CPC .............. *A61B 5/361* (2021.01); *A61B 5/35* (2021.01); *A61B 5/352* (2021.01); *A61B 5/366* (2021.01); *A61B 5/7232* (2013.01)

(58) Field of Classification Search
CPC .......................... A61B 5/352; A61B 5/7232
See application file for complete search history.

(56) References Cited

U.S. PATENT DOCUMENTS

| 6,236,882 B1 | 5/2001 | Lee et al. |
| 6,347,245 B1 | 2/2002 | Lee et al. |

(Continued)

FOREIGN PATENT DOCUMENTS

EP    2294978 B1 *  9/2013  ............. A61B 5/352

OTHER PUBLICATIONS

Addison, Paul. "Wavelet transforms and the ECG: a review." Physiological Measurement, 2005; 26: R155-R199.

(Continued)

*Primary Examiner* — Michael J D'Abreu
(74) *Attorney, Agent, or Firm* — Emory Patent Group (57) ABSTRACT

Techniques are provided for generating and processing compressed sensor data. Sensor signals can be collected using one or more sensors. The sensor signals can be compressed using a compression data structure. In some instances, the compressed signal corresponds to a sampling rate at or below the Nyquist sampling rate. The compressed signal can be compared to one or more templates. Events within the compressed signal can be detected and characterized based on the comparison.

16 Claims, 6 Drawing Sheets

(51) Int. Cl.
- *A61B 5/00*    (2006.01)
- *A61B 5/35*    (2021.01)
- *A61B 5/352*   (2021.01)
- *A61B 5/366*   (2021.01)

(56) References Cited

U.S. PATENT DOCUMENTS

| | | | |
|---|---|---|---|
| 9,345,414 B1* | 5/2016 | Bardy | A61B 5/339 |
| 2003/0013978 A1* | 1/2003 | Schlegel | A61B 5/349 |
| | | | 600/509 |
| 2007/0260151 A1* | 11/2007 | Clifford | A61B 5/7264 |
| | | | 600/509 |
| 2013/0289424 A1 | 10/2013 | Brockway et al. | |
| 2016/0360977 A1 | 12/2016 | Salehizadeh et al. | |
| 2017/0156678 A1* | 6/2017 | Lim | A61B 5/7232 |

OTHER PUBLICATIONS

Mamaghanian et al. "Compressed Sensing for Real-Time Energy-Efficient ECG Compression on Wireless Body Sensor Nodes." IEEE Transactions on Biomedical Engineering, 2011; 58(9): 2456-2466.
Zhang et al. "Compressed Sensing for Energy-Efficient Wireless Telemonitoring of Noninvasive Fetal ECG Via Block Sparse Bayesian Learning." IEEE Transactions on Biomedical Engineering, 2013; 60(2): 300-309.
International Search Report and Written Opinion for International Application No. PCT/US2018/023853 dated Jul. 18, 2018.

\* cited by examiner

METHODS AND SYSTEMS FOR AUTOMATICALLY DETECTING EVENTS BASED ON ECG SIGNALS DETERMINED FROM COMPRESSED SENSED MEASUREMENTS

CROSS-REFERENCE TO RELATED APPLICATIONS

This application is the National Stage of International Application No. PCT/US2018/023853 filed Mar. 22, 2018, which claims the benefit of U.S. Provisional Application No. 62/475,198 filed Mar. 22, 2017. The entirety of each of these applications is hereby incorporated by reference for all purposes.

FIELD OF INVENTION

The present disclosure relates generally to techniques for generating and using compressed data for event detection.

BACKGROUND

The quantity and complexity of data collected by sensors continued to dramatically increase in time. Despite advancements in storage devices and processing speed, resource consumption associated with the collected continues to be a concern. This is particularly true as the resolution of monitored data increases.

SUMMARY

In some instances, a heart monitor device is provided that includes one or more sensors, one or more data processors, and a non-transitory computer readable storage medium containing instructions. When the instructions are executed on the one or more data processors, the instructions cause the one or more data processors to perform actions including generating an electrocardiogram (ECG) signal based on one or more cardiac signals. Each cardiac signal of the one or more cardiac signals includes a signal collected via a sensor of the one or more sensors. The actions include retrieving a compression data structure and compressing the ECG signal using the compression data structure to produce a compressed ECG signal. The compressed ECG signal retains information indicating timings of R-peaks. The actions further include outputting the compressed ECG signal or data characterizing the compressed ECG signal.

In some instances, the actions can further include accessing one or more ECG templates associated with one or more types of ECG events. Each ECG template of the one or more ECG templates can correspond to compressing a signature of a type of ECG event of the one or more types of ECG events using the compression data structure. The actions can also include comparing the compressed ECG signal to each of the one or more ECG templates and identifying, based on the comparison, one or more parts of the compressed ECG signal that corresponds to a particular type of ECG event of the one or more types of ECG events. The actions can further yet include outputting characterization data that is indicative of the particular type of ECG event.

In some instances, a method is provided that includes collecting, at a heart monitor device, one or more cardiac signals, each cardiac signal of the one or more cardiac signals being collected via a sensor of the heart monitor device. The method can also include generating, at the heart monitor device, an ECG signal based on the one or more cardiac signals, retrieving a compression data structure, and compressing, at the heart monitor device, the ECG signal using the compression data structure to produce a compressed ECG signal. The compressed ECG signal retains information indicating timings of R-peaks. The method can further include outputting, from the heart monitor device, the compressed ECG signal or data characterizing the compressed ECG signal.

In some instances, the method also includes accessing one or more ECG templates associated with one or more types of ECG events. Each ECG template of the one or more ECG templates can correspond to compressing a signature of a type of ECG event of the one or more types of ECG events using the compression data structure. The method can further include comparing the compressed ECG signal to each of the one or more ECG templates and identifying, based on the comparison, one or more parts of the compressed ECG signal that corresponds to a particular type of ECG event of the one or more types of ECG events. The method further yet include outputting characterization data that is indicative of the particular type of ECG event.

The following detailed description together with the accompanying drawings will provide a better understanding of the nature and advantages of the present invention.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes can be made in the function and arrangement of elements without departing from the spirit and scope as set forth in the appended claims.

Figure 1:
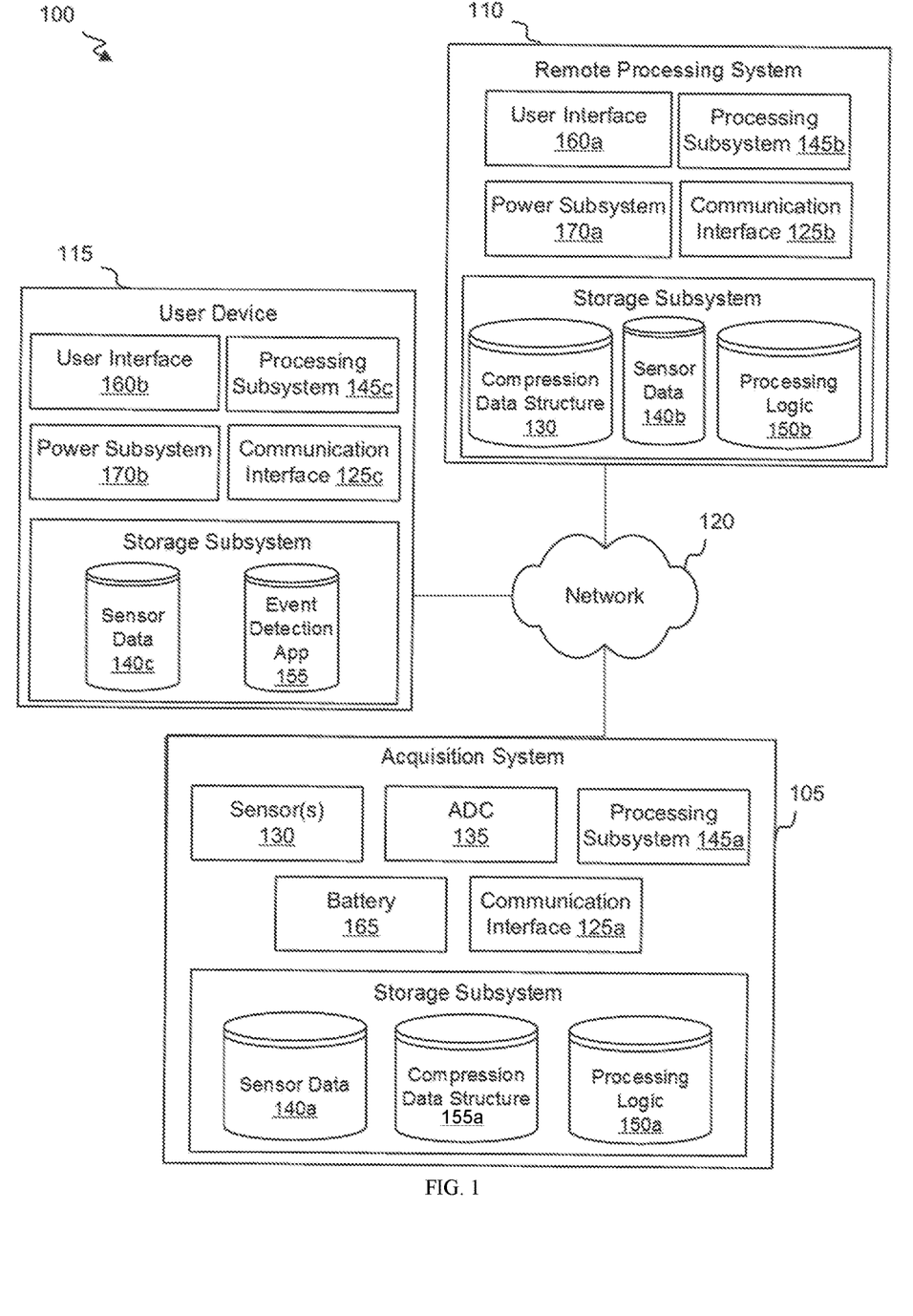
FIG. 1 shows an interaction system for collecting and using compressed data in accordance with some embodiments of the invention.

FIG. 1 shows an interaction system 100 for collecting and using compressed data in accordance with some embodiments of the invention. Interaction system 100 includes an acquisition system 105, a remote processing system 110 (e.g., one or more cloud computing systems, one or more servers, one or more computers, one or more user devices, etc.) and a user device 115 (e.g., a computer, tablet, smart phone, or smart wearable), which may communicate to each other over a network 120 (e.g., the Internet, a local area network, a wide area network, a short-range network, a Bluetooth® network, etc.). Specifically, each of acquisition system 105, remote processing system 110 and user device 115 can include one or more communication interfaces 125a, 125b and 125c, respectively, configured to transmit and receive communications over network 120. One or more of communication interfaces 125a, 125b and 125c can include an antenna and supporting circuitry to support wireless data communication (e.g., using Bluetooth®, Bluetooth Low Energy, Wi-Fi, near-field communication or other wireless-communication protocol). One or more of communication interfaces 125a, 125b and 125c can include (for example) a driver circuit, modulator/demodulator, encoder/decoder and/or other analog and/or digital signal processing circuit. It will be appreciated that different device/systems may communicate differently. For example, acquisition system 105 and remote processing system 110 may communicate over a Bluetooth® network, and remote processing system 110 and user device 115 may communicate over a Wi-Fi network.

Acquisition system 105 can include one or more sensors 130 configured to collect sensor data. One or more sensors 130 can include, for example, an electrode configured to measure electrical signals (e.g., electrocardiogram (ECG) signals, electroencephalography (EEG) signals, electromyogram (EMG) signals, electrooculography (EOG) signals, or other biosignal). The one or more sensors can include (for example) a differential amplifier to output an amplified difference between signals collected at two electrodes. The one or more sensors can be configured, for example, to detect various movement characteristics. For example, the one or more sensors can include an accelerometer and/or gyroscope. The one or more sensors can be configured to be worn by and/or attached to a user and to collect sensor data that includes physiological data pertaining to the user. The sensor data can include time-series data or continuous data, such that at least some of the sensor data is collected across a time period. The sensor data can include analog data collected at a collection sampling rate (e.g., of at least 50 Hz, at least 100 Hz, at least 125 Hz, or at least 150 Hz).

Acquisition system 105 includes an analog-to-digital converter (ADC) 135 that can convert an analog signal output by one or more sensors 130 to a digital signal. ADC 135 can include an integrated circuit. The digital signal can include time-series data or continuous data that corresponds to a same time period as the analog signal. The digital signal can have a sampling rate that is approximately the same or different than a collection sampling rate of the analog signal. In some instances, the digital signal's sampling rate is less than the collection sampling rate and can even be equal to or less than a Nyquist sampling rate. In these instances, ADC 135 can effectively be compressing the analog signal. In some instances, the digital signal's sampling rate is greater than a Nyquist sampling rate and/or approximately the same as the collection sampling rate. In some instances, a sampling rate for the digital signal (and/or effective compression ratio) can be configurable.

In some instances, acquisition system 105 transmits the digital signal to remote processing system 110 (e.g., using communication interface 125a) for further processing and/or stores the digital signal at a sensor data store 140a.

In some instances, a processing subsystem 145a of acquisition system 105 further processes the digital signal in accordance with processing logic stored at a processing logic data store 150a. Processing subsystem 145a can be implemented as one or more integrated circuits (e.g., one or more single-core or multi-core microprocessors or microcontrollers) that can execute a variety of actions in response to corresponding instruction (e.g., program code).

The processing can include compressing the digital signal (e.g., in accordance with a compression ratio that is predefined, received via input or received from another system/device). Thus, acquisition system 105 can be configured to compress sensor data before and/or after an analog-to-digital conversion of the sensor data. In some instances, compressing the digital signal can use a sparse matrix and/or binary matrix.

Compressing the digital signal can include, for example, transforming the digital signal using a compression data structure 155a. Compression data structure 155a can include, for example, a sparse matrix and/or sparsifying basis. For example, compression data structure 155a can include multiple orthogonal wavelets (e.g., Daubechies wavelets). In some instances, compression data structure 155a is configured to compress data in accordance with a compression ratio that is at least 2:1, 3:1, 4:1 or 5:1.

In some instances, compression data structure 155a is selected or generated based on a target compression ratio. Compression data structure 155a may be generated based on training data and an iterative or non-iterative technique to identify a sparse solution to maximize recovery of particular data features. For example, compression data structure 155a can be defined as Giulia Da Poian et al 2017 *Physiol. Meas.* 38 1405 details a sensing matrix to be defined. Giulia Da Poian et al 2017 *Physiol. Meas.* 38 1405 is hereby incorporated by reference in its entirety for all purposes. Transforming the digital signal can include transforming each of multiple (overlapping or non-overlapping) time windows in the digital signal using compression data structure 155a to produce a compressed value to associate with the time window or part thereof.

In some instances, acquisition system 105 transmits the compressed digital signal to remote processing system 110 (e.g., using communication interface 125a) for further processing and/or stores the compressed digital signal at a sensor data store 140a. It will be appreciated that a size of the event data may be far less than a size of the digital signal or the analog signal. Thus, transmission and/or storage requirements can be reduced.

In some instances, processing subsystem 145a of acquisition system 105 further processes the compressed digital signal. For example, the further processing may include further transforming compressed digital signal with each of one or more templates. Each of the one or more templates can be associated with a particular data signature representing a particular physiological event (e.g., a QRS complex and/or PVC beat). The template can include, for example, a temporal pattern associated with the particular physiological event (e.g., time-varying intensity or voltage values). The temporal pattern may be represented in the template in a same compressed domain as the compressed digital signal. For example, the template may have been generated by transforming an initial temporal pattern by compression data structure 155a. The transformation can include performing one or more correlations between the template and the compressed digital signal. For example, for each of multiple data points in the compressed digital signal, a part of the template (e.g., a beginning, center or end) can be aligned with the data point such that other parts of the template are aligned to other adjacent data points in the compressed digital signal. The correlation coefficient (e.g., an R value or $R^2$ value) can indicate an extent to which the template corresponds to the portion of the compressed digital signal. By evaluating multiple (e.g., consecutive) portions of the compressed digital signal in this manner, a correlation signal can be generated. In some instances, the correlations are performed using the template and a mean-adjusted compressed digital signal. The mean-adjusted compressed digital signal can be generated by identifying a mean of the compressed digital signal and subtracting the mean from each value of the compressed digital signal.

Each template can be associated with an event threshold. When the template-transformed signal crosses the threshold, the data point can be identified as corresponding to a detection of an event of an event type associated with the event threshold. The event threshold can be (for example) predefined or derived based on the template matching. The event threshold may be defined based on a Root Mean Square (RMS) value of all or part of the correlation signal. The event threshold may be defined to be the same, or alternatively, variable across the transformed signal. For example, event threshold assessments may be performed for individual (e.g., overlapping or non-overlapping) segments of the correlation signal. For example, the event threshold may be defined so as to depend on a Root Mean Square of the correlation signal for a particular segment. In one instance, the event threshold is defined to be a fraction of a maximum or the correlation signal (e.g., across the entirety of the correlation signal). The fraction may be selected based on the Root Mean Square of the correlation signal. For example, the event threshold may be defined to be half of the maximum value of the correlation signal when the Root Mean Square of the signal within the segment is less than 0.25 and to be defined as three-quarters of the maximum value of the correlation signal when the Root Mean Square of the signal otherwise. Thus, the event threshold analysis may produce an event data structure that indicates a quantity and/or temporal data of any events detected based on the sensor data.

The event data may be refined to implement a refractory period. For example, a refractory period of at least 50 ms, 100 ms, 200 ms or 400 ms (e.g., that is or is approximately 200 ms) can be employed. The refractory period can be implemented by (for example) skipping or shifting one or more signal segments upon detecting an event. The refractory period, in some instances, can be implemented as post-processing, such that events that are associated with times less than a threshold amount are merged (e.g., and assigned to a midpoint of the times or one of the times).

In some instances, acquisition system 105 transmits the event data structure to remote processing system 110 (e.g., using communication interface 125a) for further processing and/or stores the event data structure at a sensor data store 140a. It will be appreciated that a size of the event data may be far less than a size of the compressed digital signal, the digital signal or the analog signal. Thus, transmission and/or storage requirements can be reduced.

The event data may further or alternatively be refined based on an expected event characteristic (e.g., pattern or frequency). For example, a post-processing may detect when an interval between consecutive events is greater than an interval threshold defined based on other inter-event intervals (e.g., 1.5 times an average inter-event interval across the event data). Upon such detection, the event threshold for the event detection may be reduced and a segment may be redefined as one between the consecutive events. The event-detection process can then be repeated for the segment.

In some instances, an event detection can itself represent an abnormality with the analog signal. In some instances, event data can be further processed (e.g., by processing subsystem 145a of acquisition system 105) to determine whether the analog signal includes an abnormality. For example, the processing can include identifying a metric that characterizes a frequency of the events, variability of intervals between successive events, variability of frequency of the events, one or more intervals between successive events, and/or a quantity of events. The metric may then be compared to an abnormality threshold (e.g., a predefined abnormality threshold), where exceeding the abnormality threshold can be indicative of a physiological abnormality (e.g., fibrillation, heart rate variability, etc.).

Abnormality data can identify (for example) a type of abnormality detected, a time within the analog signal or digital signal associated with the abnormality, and/or a magnitude of the abnormality (e.g., the metric or an extent to which the metric exceeded the abnormality threshold).

In some instances, acquisition system 105 transmits the abnormality data to remote processing system 110 and/or user device 115 (e.g., using communication interface 125a). The transmission may, for example, trigger an alert to be presented. It will be appreciated that a size of the abnormality data may be far less than a size of the event data structure, the compressed digital signal, the digital signal or the analog signal. Thus, transmission and/or storage requirements can be reduced.

In some instances, some or all of the processing of an analog signal (or other data derived therefrom) is performed at remote processing system 110 instead of at acquisition system 105. For example, a processing subsystem 145b at remote processing system 110 can use compression data structure 155b to compress the digital signal. As another (alternative or additional) example, processing subsystem 145b at remote processing system 110 can use one or more templates to generate a correlation signal, can detect any events (e.g., using an event threshold) and/or generate an event data structure and/or can generate an event data structure. As another (alternative or additional) example, processing subsystem 145b at remote processing system 110 can process the event data structure to detect any abnormalities. Processing subsystem 145b can be implemented as one or more integrated circuits (e.g., one or more single-core or multi-core microprocessors or microcontrollers) that can execute a variety of actions in response to corresponding instruction (e.g., program code).

Remote processing system 110 can store various data at a sensor data store 140b managed by remote processing system 110. For example, sensor data store 140b can store a digital sensor signal, compressed digital signal, correlation signal, event data structure and/or abnormality data.

Processing subsystem 145b of remote processing system 110 can be configured to evaluate one or more alert conditions based on, for example, the event data structure and/or abnormality data. For example, the one or more alert conditions can indicate that an alert communication is to be transmitted to a user device when any abnormality is detected based on data associated with the user device. The alert communication can (for example) identify acquisition system 105 and/or a sensor of one or more sensors 130 associated with the analog signal that produced the abnormality detection. The alert communication can identify (for example) a type of the abnormality, a time of the abnormality, a magnitude associated with the abnormality, etc.

In some instances, an uncompressed digital signal can be reconstructed using a compressed digital signal (e.g., at remote processing system 110 and/or user device 115). The reconstruction can be performed using a Gaussian dictionary, such as using a technique detailed in Da Poian G, Bernardini R, Rinaldo R. Gaussian dictionary for compressive sensing of the ECG signal. In Biometric Measurements and Systems for Security and Medical Applications (BIOMS) Proceedings, 2014 IEEE Workshop on 2014 Oct. 17 (pp. 80-85). IEEE and/or Da Poian G, Bernardini R, Rinaldo R. Separation and analysis of fetal-ecg signals from compressed sensed abdominal ecg recordings. IEEE Transactions on Biomedical Engineering. 2016 June; 63(6):1269-79. Each of Da Poian G, Bernardini R, Rinaldo R. Gaussian dictionary for compressive sensing of the ECG signal. In Biometric Measurements and Systems for Security and Medical Applications (BIOMS) Proceedings, 2014 IEEE Workshop on 2014 Oct. 17 (pp. 80-85). IEEE and/or Da Poian G, Bernardini R, Rinaldo R. Separation and analysis of fetal-ecg signals from compressed sensed abdominal ecg recordings. IEEE Transactions on Biomedical Engineering. 2016 June; 63(6):1269-79 is hereby incorporated by reference in its entirety for all purposes.

In one instance, the reconstructed signal can be used to generate a presentation that identifies higher resolution sensor data that corresponds to a detected abnormality. To illustrate, compressed data may be used to detect an abnormality at time and reconstructed sensor data can then be generated for a time window that includes (e.g., and is centered on) time $t_i$. This reconstructed data can be presented at a user device as part of an abnormality alert.

In one instance, the reconstructed signal can be used to (for example) assess whether an alert is to be issued (e.g., based on whether an alert condition is satisfied based on the reconstructed signal). As one example, a template may be generated that corresponds to an uncompressed event signature (e.g., a QRS complex). A correlation signal can then be generated based on the template and reconstructed signal, and an abnormality may be detected (for example) when the correlation signal exceeds a threshold.

Though this type of processing can require additional resources as compared to performing similar processing using a compressed signal, use of the compressed signal may conserve bandwidth for a transmission, resources at an acquisition device (e.g., potentially having more limited processing and/or storage resources), etc. Further, the more intensive processing can then be performed by one or more machines having more extensive processing and/or storage resources.

An alert communication can be configured to be processed by an event-detection app 155 installed at user device 115. In some instances, all or part of a signal is also transmitted to user device 115 (e.g., from remote processing system 110). For example, part of an analog or digital signal associated with the abnormality can be transmitted. User device 115 can store the all or part of the signal in a sensor data store 140*c*.

A processing subsystem 145*c* at user device 115 can execute code from event detection app 155 to process the alert communication. Processing subsystem 145*c* can be implemented as one or more integrated circuits (e.g., one or more single-core or multi-core microprocessors or microcontrollers) that can execute a variety of actions in response to corresponding instruction (e.g., program code).

The processing can include generating an output in response to the alert communication. The output can include, for example, a visual, audio and/or haptic that is indicative of detection of the abnormality. The output may identify data from the alert communication (e.g., indicating a type and/or time of the abnormality). In some instances, a portion of the analog or digital signal that corresponds to the abnormality can be presented.

In some instances, user device 115 is associated with a same person from whom physiological data was collected by acquisition system 105. In some instances, user device 115 is associated with a different person (e.g., a medical care provider). In these instances, an alert may also identify acquisition system 105 and/or the person from whom the physiological data was collected.

In some instances, remote processing system 110 and/or user device 115 includes a user interface 160*a*, 160*b*, which can be configured to present outputs and/or receive inputs. For example, user interface 160*a* and/or 160*b* can include a display, touch screen, cursor control (e.g., mouse or trackpad), speaker, microphone, haptic output and/or camera. In some instances, at least part of user interface 160*a* and/or 160*b* can be configured to present an alert of detection of abnormality. In some instances, at least part of user interface 160*a* and/or 160*b* can be configured to receive a specification as to a processing that is to be performed (e.g., for which abnormalities monitoring is to be performed, one or more threshold values, one or more time periods for which monitoring is to be performed, etc.). When the specification pertains to processing being performed at another device/system, user device 115 or remote processing system 110 can transmit the specification to the other device/system.

Each of acquisition system 105, remote processing system 110 and user device 115 can include a power source or power subsystem to receive power from an external source. In the depicted instance, acquisition system includes a battery 165 (e.g., a rechargeable battery), and remote processing system 110 and user device 115 include a power subsystem 170*a*, 170*b*. Power subsystem 170*a* and/or 170*b* can include (for example) a port to receive a charging cord and/or a battery. One or more of acquisition system 105, remote processing system 110 and user device 115 can further include a power management subsystem that controls power to be supplied to various device components (e.g., processing tasks). It will be appreciated that processing and transmitting larger data sets can consume more resources (e.g., processing power, power, bandwidth, etc.) as compared to small data sets. Thus, the compression techniques disclosed herein can reduce resource consumption. In some instances, a degree of compression (e.g., compression ratio) is determined based on power availability (e.g., a charge remaining in a battery or whether a power source is a battery or AC source), where higher compression is performed in response to (for example) lower battery charge levels and/or reliance on a battery power source over an AC power source.

It will be appreciated that each of acquisition system 105, remote processing system 110 and user device 115 can include a storage subsystem, which can include one or more of the disclosed data stores, an operating system and/or other information and/or programs. The storage subsystem can be implemented, e.g., using magnetic storage media, flash memory, other semiconductor memory (e.g., DRAM, SRAM), or any other non-transitory storage medium, or a combination of media, and can include volatile and/or non-volatile media.

It will be appreciated that multiple variations of interaction system 100 are contemplated. For example, one, more or all of the components and/or functionalities disclosed as being included in and/or associated with remote processing system 110 may be included in acquisition system 105. Thus, for example, an interaction system need not include a separate remote processing system and may instead include a more sophisticated acquisition system 105 that communicates with user device 115. In some instances, interaction system 100 continues to include a remote processing system 110 that is separate from acquisition system 105, but the systems may be connected via a different type of network (e.g., a wired and/or local area network connection) than a network by which one or both of remote processing system 110 and acquisition system 105 communicates with user device 115.

Figure 2:
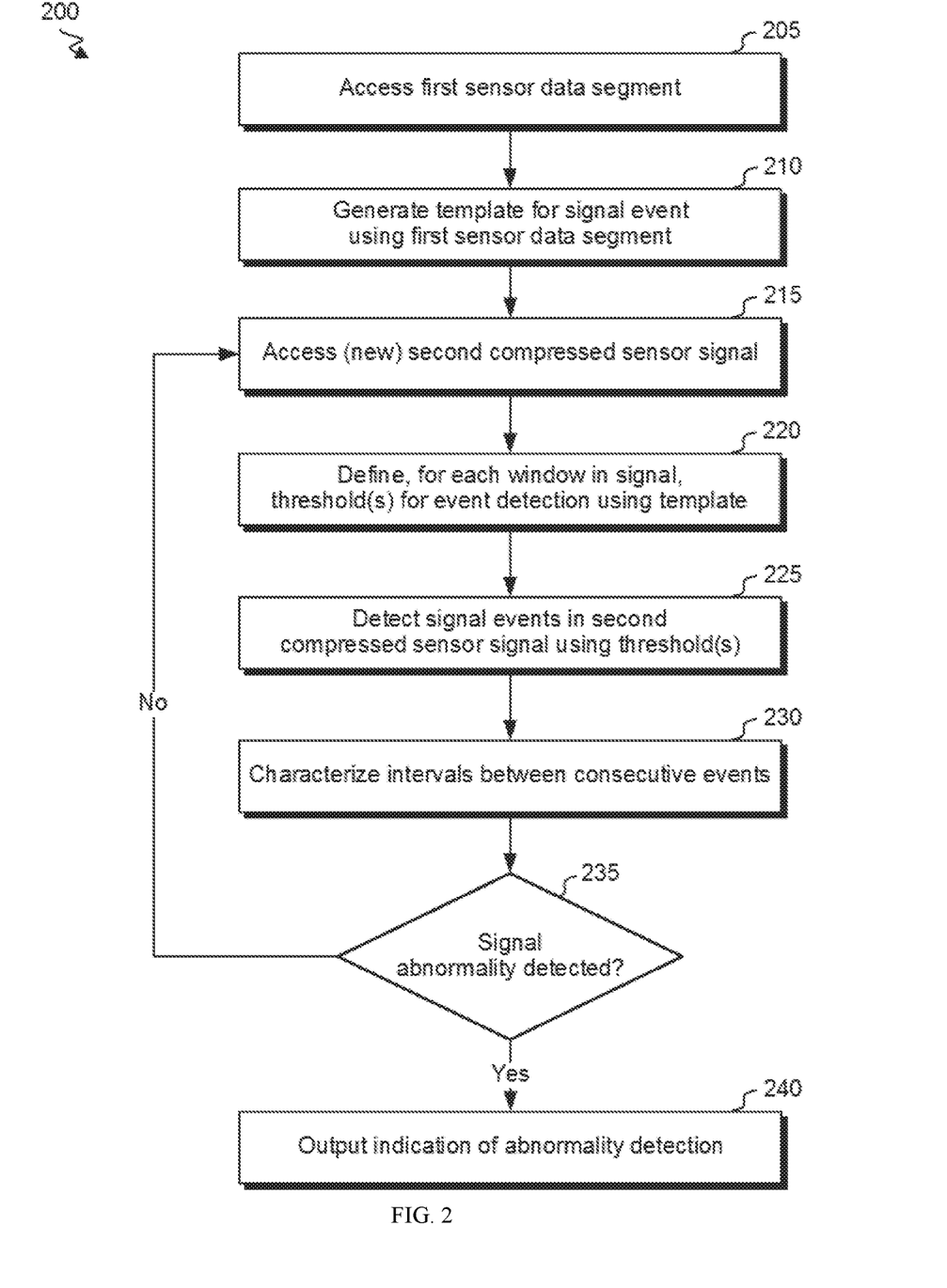
FIG. 2 shows a flowchart for a process of using compressed data to detect signal abnormalities in accordance with some embodiments.

FIG. 2 shows a flowchart for a process of using compressed data to detect signal abnormalities in accordance with some embodiments. Part or all of process 200 can be performed on an acquisition system, remote processing system and/or user device.

Process 200 begins at block 205 where a first sensor data segment is accessed. The first sensor data segment can include a digital representation of data collected by a sensor over a first time period. The first time period may be of a predefined duration (e.g., less than or about 10 minutes, 5 minutes, 1 minute or 30 seconds). The first sensor data segment can include physiological data, such as ECG data.

At block 210, a template is generated for a signal event using the first sensor data segment. The template may be generated by detecting one or more events within the first sensor data segment (e.g., as indicated by the data crossing a predefined threshold and/or via a peak detection), extracting a window of data temporally related to the event from the data segment (e.g., and padding the window with zero's or a mean or median value if needed), and averaging the windows of data. For example, for ECG data, a peak-detection algorithm is applied to the first segment. The peak-detection algorithm can include a smoothing preprocessing. The peak-detection can include detecting whether the first segment crosses a first crossing threshold (in a first direction) and/or whether the first segment crosses a second (different or same) crossing threshold (in a second opposite direction). In some instances, a first crossing and the second crossing are to be within a predefined time period in order for a peak to be detected. In some instances, the threshold assessment is performed on a processed version of the first segment (e.g., a smoothed version, a first derivative, a second derivative, etc.).

Each time the data crosses the predefined threshold, a "beat" or "QRS complex" event can be defined for the threshold-crossing time. For each beat, the window of data can correspond to ECG data that starts at a first time (that is a first predefined time before the threshold crossing) and ends at a second time (that is a second predefined time after the threshold crossing). The windows can then be averaged to produce a template for the QRS complex event. Thus, the template can include an event-triggered average. The averaged event-triggered data may be compressed using a data compression structure. It will be appreciated that, in some instances, multiple templates can be generated. Each template can (for example) correspond to a different type of event.

At block 215, a second compressed sensor signal is accessed. The second compressed sensor signal can include a compressed version of a second sensor data segment. The compression of the second compressed sensor signal may have been performed (e.g., at an acquisition system) using a same data compression structure as used to compress the template.

The second sensor data segment can include a digital representation of data collected by a sensor over a second time period. The second time period can include a time period after the first time period. In some instances, each of the first time period and second time period correspond to a respective part of a single data-collection session. In some instances, a sensor collects data continuously over an extended time period, and various second sensor data segments are iteratively assessed (e.g., while another second sensor data segment is being collected). The second sensor data segment can include physiological data, such as ECG data.

At block 220, one or more thresholds are defined for event detection using the template. The threshold can further depend on the second sensor data segment and/or the second compressed sensor signal. In some instances, the threshold is defined based on a maximum correlation value and a root-mean square value of one or more correlation between part of all of the second compressed sensor signal and the template.

For example, the second compressed sensor signal can first be preprocessed by calculating a mean (e.g., or median or mode) of the second compressed sensor signal and subtracting the mean from the second compressed sensor signal. A correlation vector can then be generated by performing a correlation between the mean-subtracted second compressed sensor signal and the template. A maximum value of the correlation can be identified. The threshold can be defined based on this maximum value. For example, the threshold can be defined to be a fraction of the maximum value.

In some instances, event detection begins by defining multiple windows in the second compressed sensor signal and separately evaluating each window for a potential event. A size of the windows can be less than a size of the second compressed sensor signal. The multiple windows may be non-overlapping adjacent windows. In some instances, the multiple windows are overlapping. A threshold may be generally defined to apply to all windows or may be defined for each individual window (e.g., based on data within the second compressed sensor signal in the window).

A threshold can be defined for each window of multiple windows in the second compressed sensor signal. For example, a threshold may be defined based on a root mean square of a correlation between a part of the second compressed sensor signal (the part corresponding to the window) and the template and further on the maximum value of the correlation between the whole second compressed sensor signal and the template. The root mean square value may be used to identify a factor by which the maximum value is multiplied to produce the threshold. A relationship between the root mean square value may be (for example) monotonic, a real function, a stepwise function etc. For example, the factor may be set to 0.75 when the root mean square value is greater than 0.25 and set to 0.5 otherwise.

At block 225, signal events are detected in the second compressed sensor signal using a threshold. The detection can include a window-by-window analysis. The detection can be based on a correlation signal generated based on at least part of the second compressed sensor (e.g., a part corresponding to the window) and the template. The detection can include determining whether the correlation signal crosses a threshold (e.g., a threshold defined for the window or a general threshold).

In some instances, event detection is refined after a window-by-window event detection. The refinement may include adding or deleting one or more events based on inter-event intervals. For example, the refinement can include introducing a refractory period, merging events that are close in time, adding an event upon detecting a cyclical event pattern with a missing cycle, implementing a cost function to determine whether to add or remove any events (e.g., based on expected inter-event spacing), etc.

At block 230, one or more intervals between consecutive events are characterized. Specifically, each of the events detected in the second compressed sensor signal can be associated with an event time that corresponds to a time within the second compressed sensor signal. An interval duration can be identified between each consecutive pair of intervals. Thus, if there are n events detected, there can be n−1 intervals identified. The characterization of the intervals can include (for example) determining a minimum interval, a maximum interval, an interval variability, a median interval, a mean interval, an extent to which an interval pattern corresponds to a target (e.g., normal) interval pattern, etc.

At block 235, it is determined whether a signal abnormality is detected based on the interval characterization. The determination can include (for example) determining whether an interval statistic is above an interval threshold and/or whether an interval statistic is below an interval threshold. When no abnormality is detected, process 200 returns to block 215 to access and process a new second compressed sensor signal. Thus, for example, determining whether the signal abnormality is detected can include determining whether an abnormality condition is satisfied (e.g., based on interval data).

When an abnormality is detected, process 200 proceeds to block 240 where an indication of the abnormality detection is output. For example, a communication may be generated and transmitted (e.g., to a user device or device of a care provider), and/or a notification can be generated and presented. The communication and/or notification can be indicative of an abnormality detection, identify a type of physiological event associated with the abnormality, include a part of the second compressed sensor signal (and/or of a correlation signal or interval data structure) that corresponds to the abnormality, identify a user or device from which the second sensor signal was collected, etc. In some instances, abnormalities are tracked over a time period, such that a statistic as to a frequency or count of abnormalities can be generated and included in the communication and/or notification.

Figure 3A:
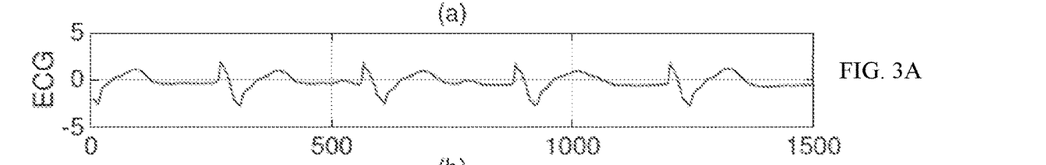
FIGS. 3A-3C show example time series corresponding to a compression-based processing.
Figure 3B:
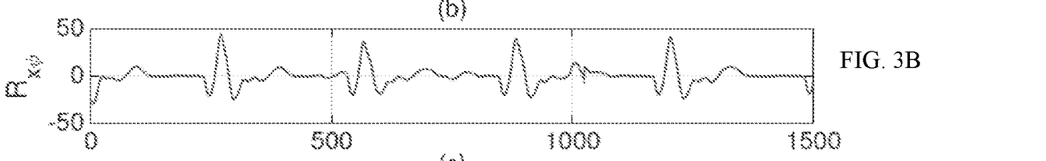
Figure 3C:
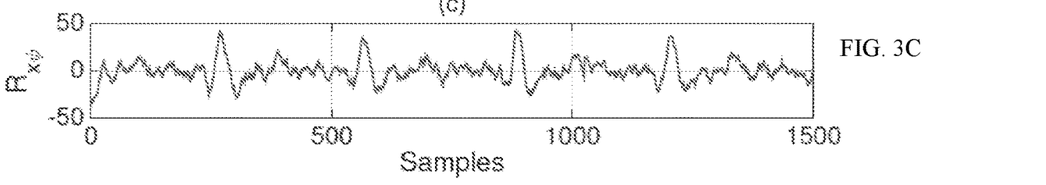

FIGS. 3A-3C show example time series corresponding to a compression-based processing. FIG. 3A shows an ECG signal collected at 3660 Hz. FIG. 3B shows a correlation signal that was generated by correlating the ECG signal from FIG. 3A with a template generated based on QRS complex signals. In a separate correlation analysis, the ECG signal was compressed using a 2:1 compression ratio. The compressed signal was correlated with a compressed version of the template. FIG. 3C shows the correlation signal generated using these compressed data sets. As can be seen, the peaks are pronounced in both correlation signals, despite the FIG. 3C correlation signal having been generated using a fraction of the data (and thereby reducing resource expenditure).

Figure 4A:
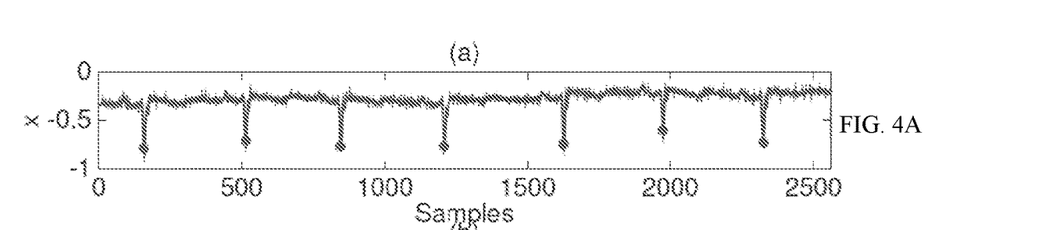
FIGS. 4A-4D show example time series and a template corresponding to a compression-based processing.
Figure 4B:
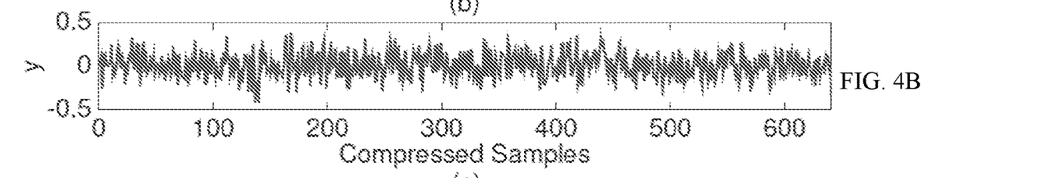
Figure 4C:
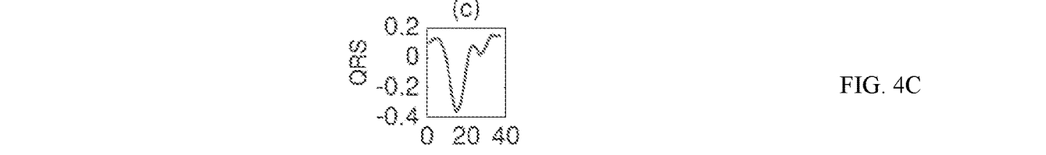
Figure 4D:
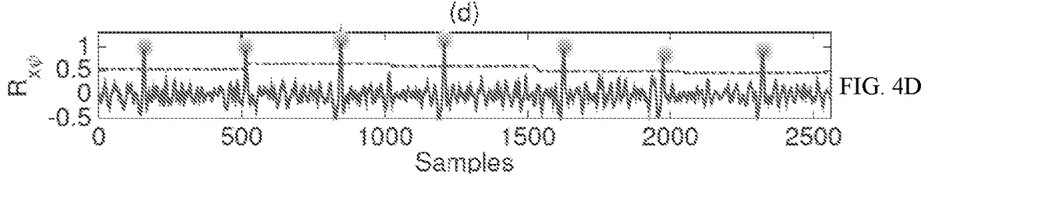

FIGS. 4A-4D show example time series and a template corresponding to a compression-based processing. FIG. 4A shows an original ECG signal. FIG. 4B shows a compressed version of the ECG signal, where the compression was performed using a 4:1 compression ratio. FIG. 4C shows a template used for event detection. The template corresponds to a QRS complex. The template includes one generated by generating an initial template based on uncompressed signals and then compressing the template using a 4:1 compression ratio. FIG. 4D shows a correlation signal generated using the template and the compressed version of the ECG signal. As shown, the above-threshold peaks remain pronounced despite the substantial compression.

Figure 5:
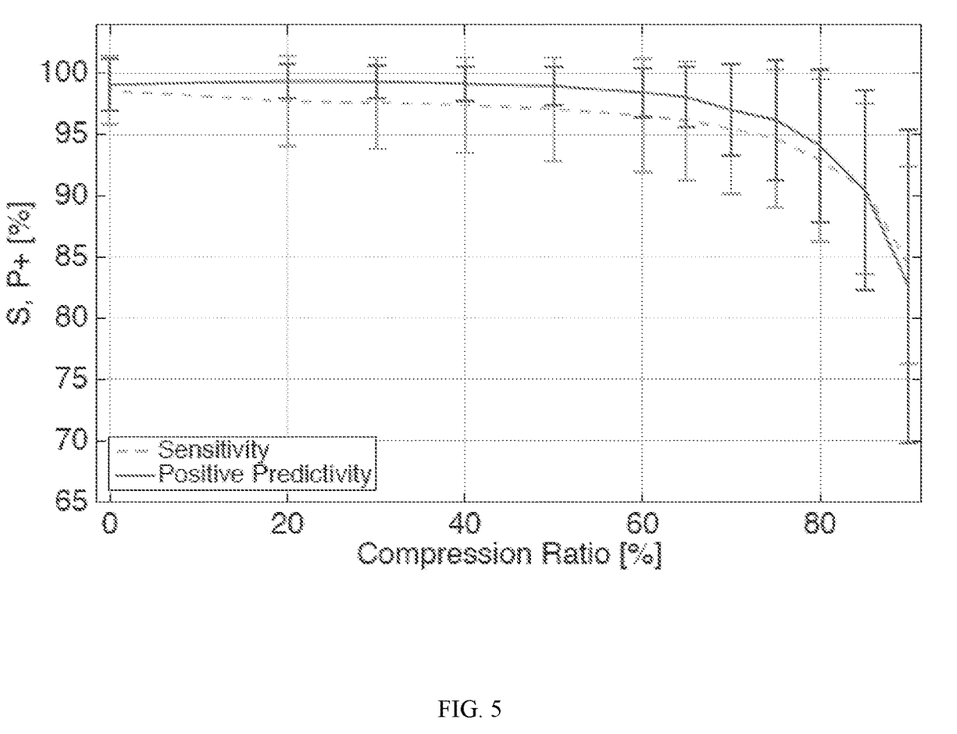
FIG. 5 shows an example illustration of a dependence of accuracy of event detection on compression ratio.

FIG. 5 shows an example illustration of a dependence of accuracy of event detection on compression ratio. In this instance, the events and template were defined to correspond to QRS complexes. An uncompressed ECG signal and uncompressed template were initial used to detect each QRS complex in the signal. Then each of the ECG signal and template were compressed by various compression ratios, and event detection was performed using the compressed data sets. The events detected using the compressed data (for each compression ratio) was compared to the events detected using the uncompressed data to identify a quantity of true positives (TP), a quantity of false negatives (NP) and a quantity of false positives (FP). A Sensitivity metric (Se) and Positive Productivity metric (P+) was calculated for each compression ratio, using the following:

Accuracy of QRS Detection at Various Compression Ratios Evaluated Using Sensitivity (Se) and Positive Productivity (P+):

$$Se = \frac{TP}{TP + FN} 100,$$

$$P+ = \frac{TP}{TP + FP} 100.$$

FIG. 5 shows the Sensitivity metrics and Positive Productivity metrics as a function of compression ratio. As shown, the quality of the event detection remains high even at high compression ratios.

Figure 6:
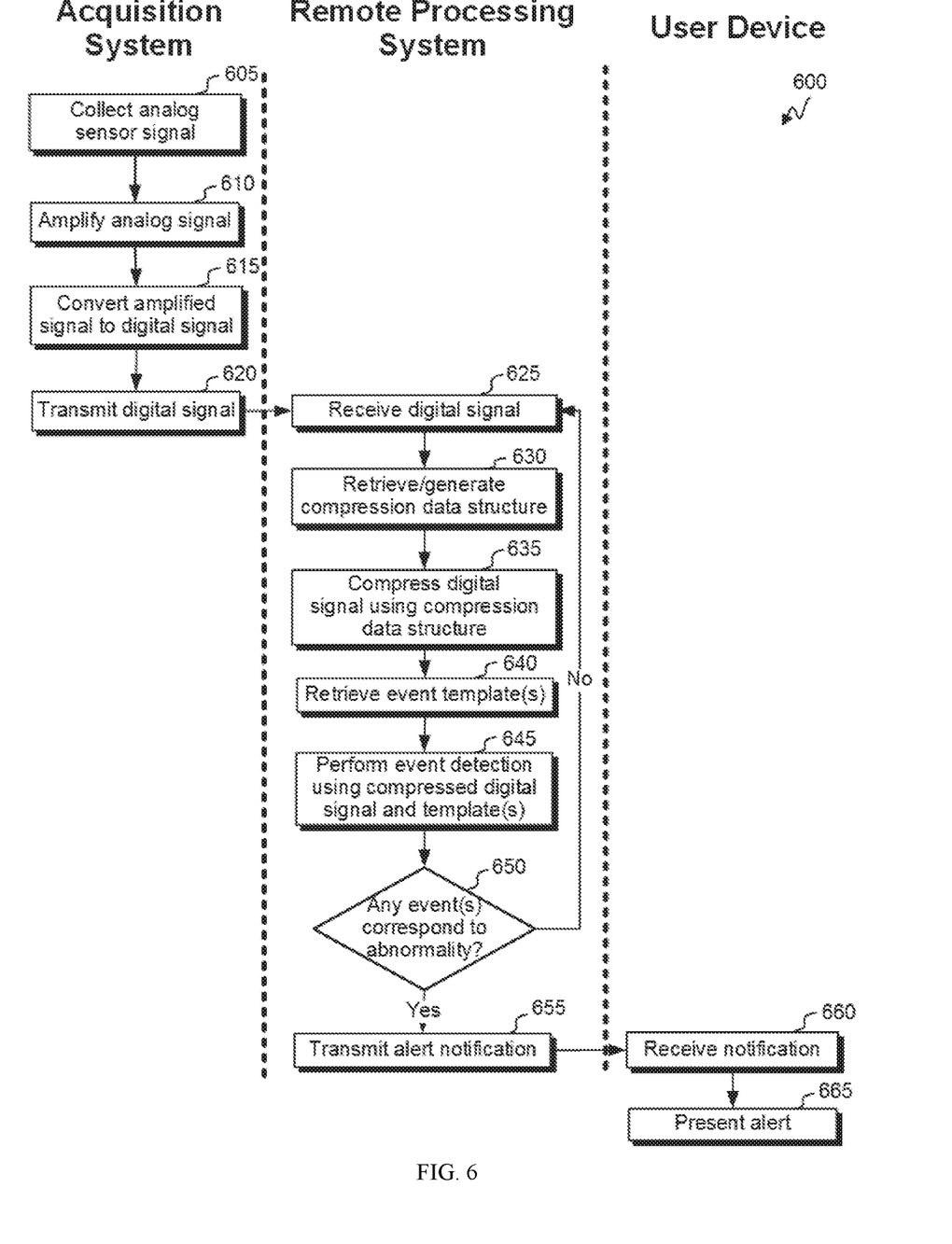
FIG. 6 shows a flow diagram of a process for collecting and using compressed data in accordance with some embodiments.

FIG. 6 shows a flow diagram of a process for collecting and using compressed data in accordance with some embodiments. Various processing of sensor data can be performed after different devices within a system architecture. FIG. 6 shows one example of distributed processing and communications.

At block 605, an acquisition system collects an analog sensor signal. For example, the analog sensor signal can include an ECG signal collected using one or more electrodes. At block 610, the acquisition signal amplifies the analog signal. At block 615, the amplified signal is converted to a digital signal. At block 620, the digital signal is transmitted to a remote processing system, which receives the digital signal at block 625.

At block 630, the remote processing system retrieves or generates a compression data structure. The compression data structure can be selected or generated based on (for example) a target compression ratio. At block 635, the remote processing system compresses the digital signal using the compression data structure. At block 640, one or more event templates are retrieved. Each of the one or more event templates can correspond with a physiological event (e.g., a QRS complex). Each of the one or more event templates can include, for example, a compression of an average of a set of uncompressed signal segments that correspond to the type of events.

At block 645, the remote processing system performs event detection using the compressed digital signal and the one or more templates. For example, for each template of the one or more templates, a correlation signal can be generated to correlate the template and the compressed digital signal. A threshold that corresponds to the template can be identified, which can depend on one or more correlations between the template and one or more (e.g., compressed) sensor signals. An event can be defined as an instance where the correlation crosses the threshold. Event detection may be further refined based on (for example) analyzing the intervals between events.

At block 650, the remote processing system determines whether any of the detected events correspond to an abnormality. For example, one or more abnormality conditions may identify particular features of events and/or inter-event intervals that, if detected, are indicative of a particular abnormality. The determination may include comparing a statistic (e.g., a frequency of events or variability of inter-event intervals) to an abnormality threshold. The determination may include inputting event times or inter-event intervals to a classifier to determine whether the data corresponds to a particular abnormality.

When an abnormality is not detected, process 600 can return to block 625, where the remote processing system begins processing a new digital signal received from the acquisition system. When an abnormality is detected, process 600 continues to block 655, where an alert communication is transmitted to a user device, which receives the notification at block 660. The alert communication can (for example) indicate that an abnormality occurred, identify a type of the abnormality, identify a time and/or duration associated with the abnormality, identify a recommended action in view of the abnormality, and/or identify a person and/or device associated with the sensor data. In some instances, the alert communication includes data corresponding to the abnormality, such as a portion of the digital signal, a portion of the compressed digital signal, a portion of a correlation signal, etc.

At block 665, the user device presents an alert that corresponds to the notification. The alert can (for example) indicate that an abnormality occurred, identify a type of the abnormality, identify a time and/or duration associated with the abnormality, identify a recommended action in view of the abnormality, and/or identify a person and/or device associated with the sensor data. The alert can include a visual and/or audio alert.

By performing event detection and abnormality assessments on compressed data, resource use (e.g., processor cycles, memory usage, bandwidth, etc.) can be reduced.

Figure 7:
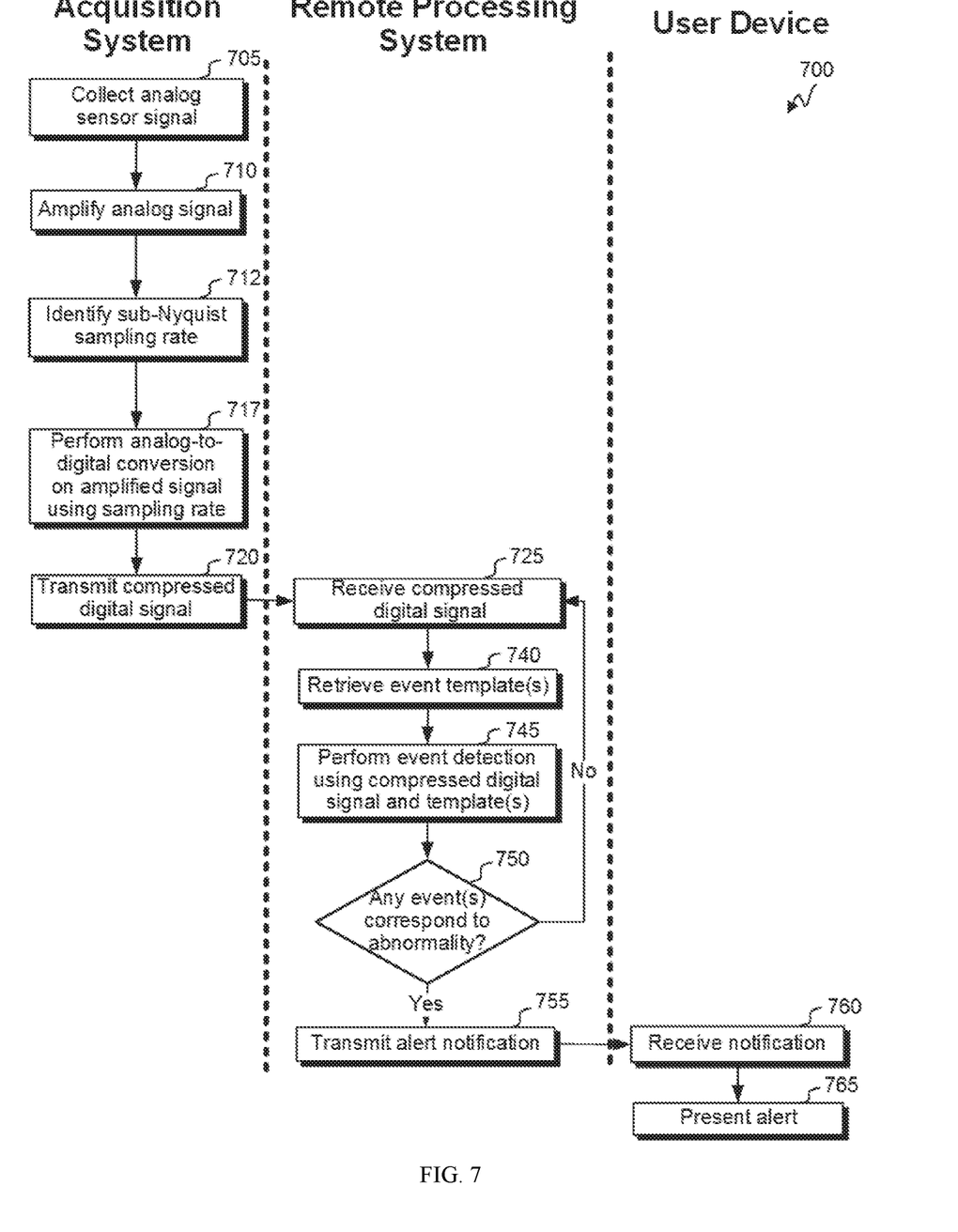
FIG. 7 shows a flow diagram of a process for collecting and using compressed data in accordance with some embodiments.

FIG. 7 shows a flow diagram of a process for collecting and using compressed data in accordance with some embodiments. Many actions from process 700 parallel actions from process 600 (depicted in FIG. 6). However, in process 700, the compression is performed prior to the analog-to-digital conversion and is performed at the acquisition system.

Specifically, at block 712, the acquisition system identifies a sampling rate that is below (or, in some instances, equal to) the Nyquist sampling rate for the signal. The analog-to-digital conversion is then performed (at block 717) using the sampling rate, such that the sampling rate of the digital signal is below (or, in some instances, equal to) the Nyquist sampling rate. Then the compressed digital signal is transmitted (at block 720) to the remote processing system.

Thus, the transmission can consume less bandwidth and/or occur more quickly than transmitting the signal without having used the lower sampling rate. Further, the compression performed at the acquisition system can reduce power consumption needed to acquire the signal.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

The invention claimed is:

1. A heart monitor device comprising:
one or more sensors;
one or more data processors; and
a non-transitory computer readable storage medium containing instructions which when executed on the one or more data processors, cause the one or more data processors to perform actions including:
  generating an electrocardiogram (ECG) signal based on one or more cardiac signals, each cardiac signal of the one or more cardiac signals being collected via a sensor of the one or more sensors;
  compressing the ECG signal using a compression data structure to produce a compressed ECG signal, wherein the compressed ECG signal retains information indicating timings of R-peaks;
  accessing one or more ECG templates associated with one or more types of ECG events, each ECG template of the one or more ECG templates corresponding to a compression of ECG signals associated with a type of ECG event of the one or more types of ECG events based on the compression data structure;
  comparing, at the heart monitor device, the compressed ECG signal to each of the one or more ECG templates;
  identifying, at the heart monitor device, based on the comparison, one or more parts of the compressed ECG signal that corresponds to a particular type of ECG event of the one or more types of ECG events; and
  outputting data corresponding to the particular type of ECG event.

2. The heart monitor device of claim 1, wherein:
an ECG template of the one or more ECG templates is associated with an ECG event representing a QRS complex; and
the identifying the one or more parts includes detecting, for each time of a set of times, that a part of the compressed ECG signal associated with the time and being of the one or more parts corresponds to a QRS complex; and
determining a heart rate based on the set of times; and
outputting the heart rate.

3. The heart monitor device of claim 1, wherein the one or more cardiac signals are signals of a particular user, and wherein the actions further include:
  collecting, using one or more same sensors as used to collect the one or more cardiac signals of the particular user, one or more initializing cardiac signals;
  generating, at the heart monitor device, another ECG signal based on the one or more initializing cardiac signals; and
  detecting one or more ECG events of the particular type of ECG event in the other ECG signal;
  generating the signature of the particular type of ECG event based on the detected ECG events, the signature thereby being specifically generated for the particular user.

4. The heart monitor device of claim 1, wherein the particular type of ECG event includes atrial fibrillation.

5. The heart monitor device of claim 1, wherein:
the compression data structure is configured to have a compression ratio of at least 2:1; and
a size of the ECG signal is at least two times a size of the compressed ECG signal.

6. The heart monitor device of claim 1, wherein the compression data structure has a first compression ratio, and the actions further include:
  generating another compression data structure based on a second compression ratio that is different from the first compression ratio;
  compressing, at the heart monitor device, another ECG signal using the other compression data structures to produce another compressed ECG signal; and
  outputting the other compressed ECG signal or data characterizing the other compressed ECG signal.

7. The heart monitor device of claim 1, wherein the outputting the compressed ECG signal or data characterizing the compressed ECG signal includes transmitting the compressed ECG signal or data characterizing the compressed ECG signal to a remote computer system.

8. A method comprising:
  collecting, at a heart monitor device, one or more cardiac signals, each cardiac signal of the one or more cardiac signals being collected via a sensor of the heart monitor device;
  generating, at the heart monitor device, an ECG signal based on the one or more cardiac signals;
  compressing, at the heart monitor device, the ECG signal using the compression data structure to produce a compressed ECG signal, wherein the compressed ECG signal retains information indicating timings of R-peaks;
  accessing one or more ECG templates associated with one or more types of ECG events, each ECG template of the one or more ECG templates corresponding to a compression of ECG signals associated with a type of ECG event of the one or more types of ECG events based on the compression data structure;
  comparing, at the heart monitor device, the compressed ECG signal to each of the one or more ECG templates;
  identifying, at the heart monitor device, based on the comparison, one or more parts of the compressed ECG signal that corresponds to a particular type of ECG event of the one or more types of ECG events; and
  outputting data corresponding to the particular type of ECG event.

9. The method of claim 8, wherein:
an ECG template of the one or more ECG templates is associated with an ECG event representing a QRS complex; and
the identifying the one or more parts includes detecting, for each time of a set of times, that a part of the compressed ECG signal associated with the time and being of the one or more parts corresponds to a QRS complex; and determining a heart rate based on the set of times; and outputting the heart rate.

10. The method of claim 8, wherein the one or more cardiac signals are signals of a particular user, and wherein the method further includes:

collecting, using one or more same sensors as used to collect the one or more cardiac signals of the particular user, one or more initializing cardiac signals;

generating, at the heart monitor device, another ECG signal based on the one or more other cardiac signals; and detecting one or more ECG events of the particular type of ECG event in the other ECG signal;

generating the signature of the particular type of ECG event based on the detected ECG events, the signature thereby being specifically generated for the particular user.

11. The method of claim 8, wherein the particular type of ECG event includes atrial fibrillation.

12. The method of claim 8, wherein generating the ECG signal includes performing an analog-to-digital conversion of the one or more cardiac signals.

13. The method of claim 8, wherein the compression data structure has a first compression ratio, and the method further comprising:

generating another compression data structure based on a second compression ratio that is different from the first compression ratio;

compressing, at the heart monitor device, another ECG signal using the other compression data structures to produce another compressed ECG signal; and outputting the other compressed ECG signal or data characterizing the other compressed ECG signal.

14. The method of claim 8, wherein:

the compression of the ECG signal comprises performing an analog-to-digital conversion of the ECG signal to produce the compressed ECG signal, the compressed ECG signal having a target sampling rate, the target sampling rate being lower than a Nyquist sampling rate for the ECG signal.

15. The method of claim 8, further comprising:

storing the compressed ECG signal at the heart monitor device.

16. The method of claim 8, further comprising:

generating a reconstructed ECG signal using the compressed ECG signal, a Gaussian dictionary and the compression data structure;

identifying, based on the reconstructed ECG signal, one or more parts of the reconstructed ECG signal that corresponds to a particular type of ECG event of the one or more types of ECG events; and outputting data corresponding to the particular type of ECG event identified based on the reconstructed ECG signal.

* * * * *